(12) United States Patent
Seki

(10) Patent No.: US 11,175,271 B2
(45) Date of Patent: Nov. 16, 2021

(54) ALLERGEN DETECTION METHOD

(71) Applicant: NISSHIN SEIFUN GROUP INC., Chiyoda-ku (JP)

(72) Inventor: Yusuke Seki, Fujimino (JP)

(73) Assignee: NISSHIN SEIFUN GROUP INC., Chiyoda-ku (JP)

( * ) Notice: Subject to any disclaimer, the term of this patent is extended or adjusted under 35 U.S.C. 154(b) by 102 days.

(21) Appl. No.: 16/318,756

(22) PCT Filed: Jul. 20, 2017

(86) PCT No.: PCT/JP2017/026179
§ 371 (c)(1),
(2) Date: Jan. 18, 2019

(87) PCT Pub. No.: WO2018/016551
PCT Pub. Date: Jan. 25, 2018

(65) Prior Publication Data
US 2019/0302081 A1    Oct. 3, 2019

(30) Foreign Application Priority Data

Jul. 21, 2016 (JP) .............................. JP2016-142994

(51) Int. Cl.
*G01N 33/02* (2006.01)
*C12Q 1/37* (2006.01)
*G01N 30/06* (2006.01)
*G01N 30/72* (2006.01)
*G01N 27/62* (2021.01)
(Continued)

(52) U.S. Cl.
CPC .............. *G01N 33/02* (2013.01); *C12Q 1/37* (2013.01); *G01N 27/62* (2013.01); *G01N 30/06* (2013.01); *G01N 30/72* (2013.01); *G01N 30/7233* (2013.01); *G01N 30/88* (2013.01); *G01N 33/68* (2013.01); *G01N 2030/027* (2013.01); *G01N 2030/067* (2013.01)

(58) Field of Classification Search
None
See application file for complete search history.

(56) References Cited

U.S. PATENT DOCUMENTS

2010/0112709 A1*  5/2010  Seki .................. G01N 33/5306
                                                           436/86

FOREIGN PATENT DOCUMENTS

JP     2013-539039 A    10/2013
JP     2014-525588 A     9/2014
(Continued)

OTHER PUBLICATIONS

Nagai et al., Report of Gifu Prefectural Research Institute for Health and Environmental Sciences 22: 1-5 (2014).*
(Continued)

Primary Examiner — Erin M. Bowers
(74) Attorney, Agent, or Firm — Oblon, McClelland, Maier & Neustadt, L.L.P.

(57) ABSTRACT

A highly-sensitive-allergen-measurement method is provided. A method for detecting an allergen in a sample comprises treating the sample with a protease, and detecting the presence or absence of an allergen-derived polypeptide in the enzymatically treated sample by a chromatographic separation analysis, wherein the allergen is one or more members selected from the group consisting of buckwheat, crustacean, milk, egg and peanut.

6 Claims, 7 Drawing Sheets
Specification includes a Sequence Listing.

(51) Int. Cl.
    *G01N 33/68* (2006.01)
    *G01N 30/88* (2006.01)
    *G01N 30/02* (2006.01)

(56) References Cited

FOREIGN PATENT DOCUMENTS

WO  WO 2012/044411 A2  4/2012
WO  WO 2013/033713 A1  3/2013

OTHER PUBLICATIONS

Takaoka et al., Proceedings of the 9th International Symposium on Buckwheat, Prague, 95-98 (2004).*
Park et al., Korean J. Plant Res. 22(3): 227-235 (2009).*
Abdel Rahman et al., Rapid Communications in Mass Spectrometry 24: 2462-2470 (2010).*
International Search Report dated Aug. 22, 2017 in PCT/JP2017/026179 filed Jul. 20, 2017.
Nagai, H. et al., "Development of a Method for Crustacean Allergens Using Liquid Chromatography/Tandem Mass Spectrometry," Journal of AOAC International, vol. 98, No. 5, 2015, pp. 1355-1365.
Korte, R. et al., "New High-Performance Liquid Chromatography Coupled Mass Spectrometry Method for the Detection of Lobster and Shrimp Allergens in Food Samples via Multiple Reaction Monitoring and Multiple Reaction Monitoring Cubed," Journal of Agricultural and Food Chemistry, vol. 64, Jul. 8, 2016, pp. 6219-6227.
Hiroyuki Nagai et al., "Development of analytical method for egg and milk allergens in processed foods by LC-MS/MS," Report of Gift Prefectural Research Institute for Health and Environmental Sciences, vol. 22, 2014, pp. 1-5 (with English summary).
Ansari, P. et al., "Selection of possible marker peptides for the detection of major ruminant milk proteins in food by liquid chromatography—tandem mass spectrometry," Analytical Bioanalytical Chemistry, vol. 399, 2011, pp. 1105-1115.
Chassaigne, H. et al., "Proteomics-Based Approach To Detect and Identify Major Allergens in Processed Peanuts by Capillary LC-Q-TOF (MS/MF)," Journal of Agricultural and Food Chemistry, vol. 55, 2007, pp. 4461-4473.
Lock, S. et al., "The Detection of Allergens in Bread and Pasta by Liquid Chromatography Tandem Mass Spectrometry," Food & Environmental, AB SCIEX, 2010, pp. 1-5.
Yano, M. et al., "Purification and Properties of Allergenic Proteins in Buckwheat Seeds," Agricultural Biological Chemistry, vol. 53, No. 9, 1989, pp. 2387-2392.
Takaoka, M. et al., "Changes in Proteome Patterns in Buckwheat Seed under Submergence," Proceeding of the 9th International Symposium on Buckwheat, Prague, 2004, pp. 95-98.
Nagai, H., "Development of a Method for Determination of Buckwheat Allergens Using Liquid Chromatography with Tandem Mass Spectrometry," Journal of AOAC International, vol. 100, No. 4, Mar. 3, 2017, pp. 1051-1057.
Rahman, A.M.A. et al., "Analysis of the allergenic proteins in black tiger prawn (*Penaeus monodon*) and characterization of the major allergen tropomyosin using mass spectrometry," Rapid Communications in Mass Spectrometry, vol. 24, 2010, pp. 2462-2470.
Partial Supplementary European Search Report dated Feb. 28, 2020, in Patent Application No. 17831067.8, 16 pages.
Nagai, H. et al., "Development of a Method for Crustacean Allergens Using Liquid Chromatography/Tandem Mass Spectrometry", XP9514171, Journal of AOAC International, vol. 98, No. 5, Sep. 2015, pp. 1355-1365.
Monaci, L. et al., "Multi-allergen detection in food by micro high-performance liquid chromatography coupled to a dual cell linear ion trap mass spectrometry", XP029043540, Journal of Chromatography A, vol. 1358, Jul. 4, 2014, pp. 136-144.
Heick, J. et al., "First screening method for the simultaneous detection of seven allergens by liquid chromatography mass spectrometry", XP028138512, Journal of Chromatography A, Dec. 23, 2010, vol. 1218, No. 7, pp. 938-943.
Japanese Office Action dated Mar. 23, 2021 in Japanese Patent Application No. 2018-528848 (with English translation), 12 pages.
Anas M. Abdel Rahman, et al., "Characterization and de Novo Sequencing of Snow Crab Tropomyosin Enzymatic Peptides by Both Electrospary Ionization and Matrix-Assisted Laser Desorption Ionization QqToF Tandem Mass Spectrometry" Journal of Mass Spectrometry, vol. 45, Mar. 2, 2010, pp. 372-381.
Min-Hwa Park, et al., Proteomic Approach of the Protein Profiles during Seed Maturation in Common Buckwheat (*Fagopyrum esculentum* Moench.), Korean Journal of Plant Resources, vol. 22, No. 3, 2009, pp. 227-235.

* cited by examiner

[Fig.1]
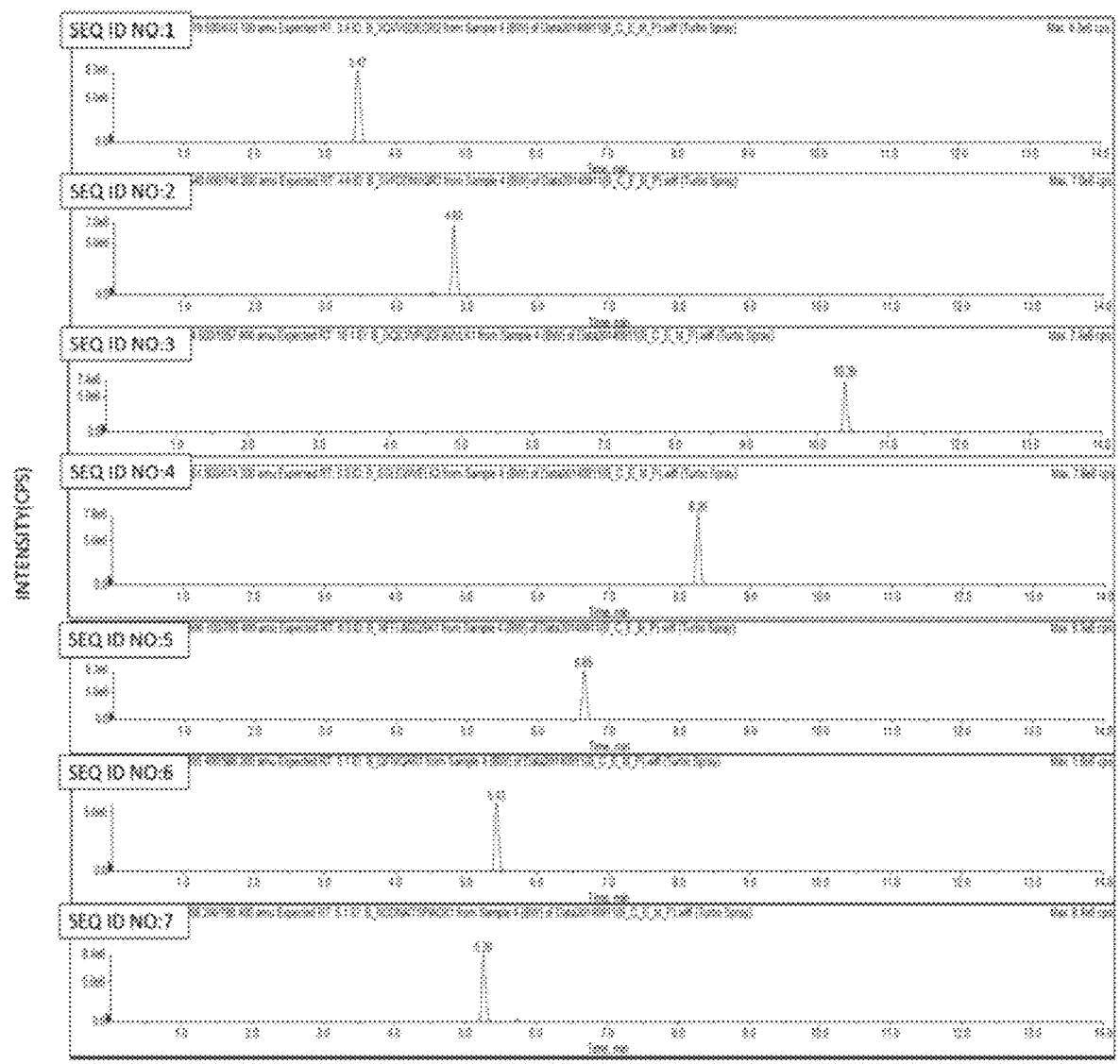

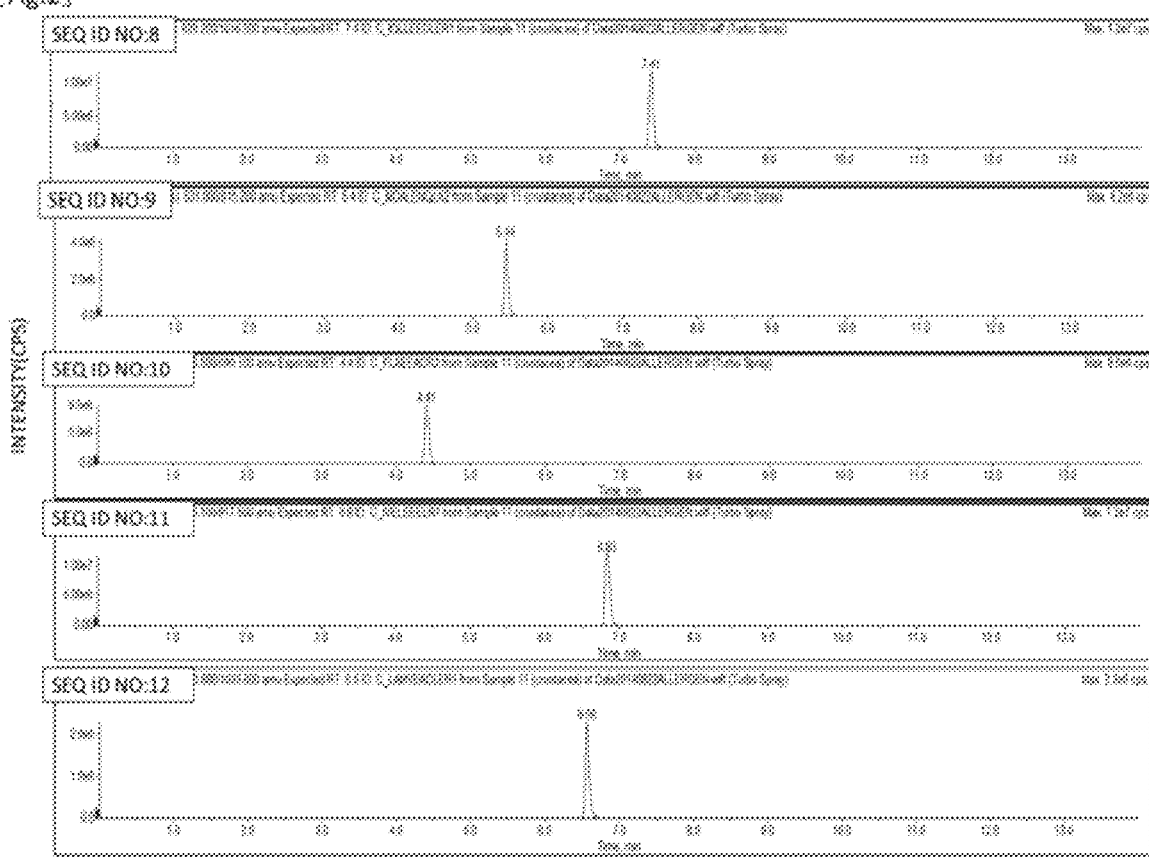
[Fig.2]

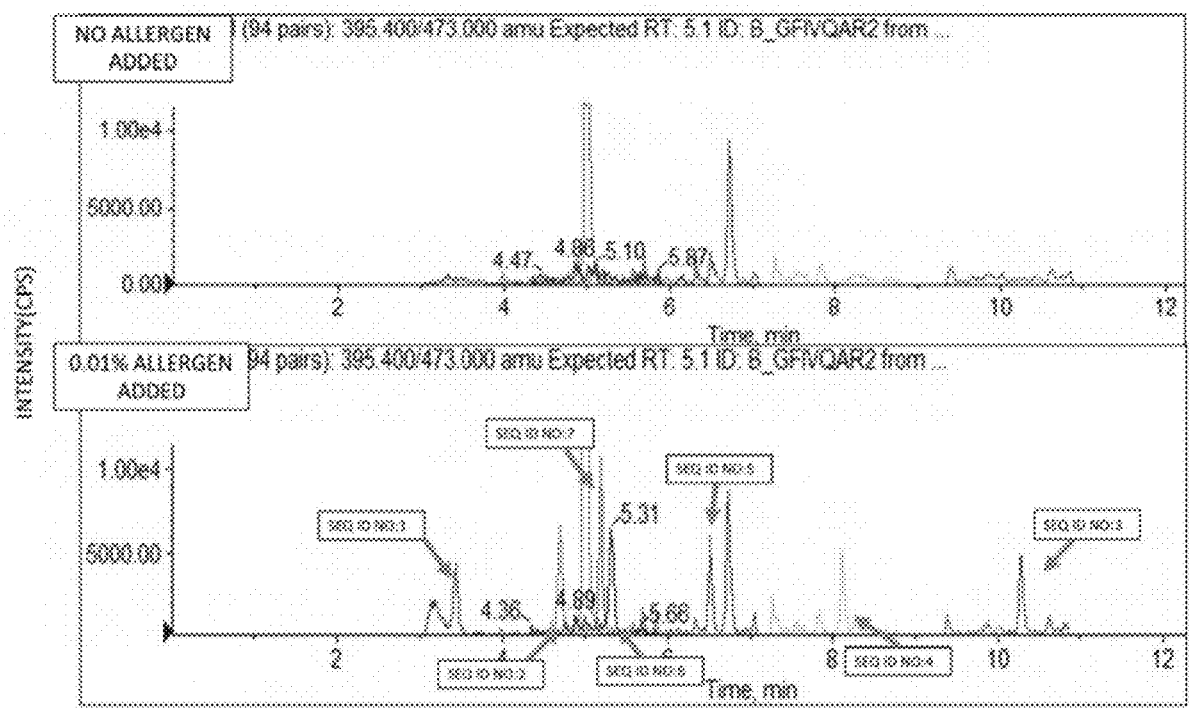
[Fig.3]

[Fig.4]
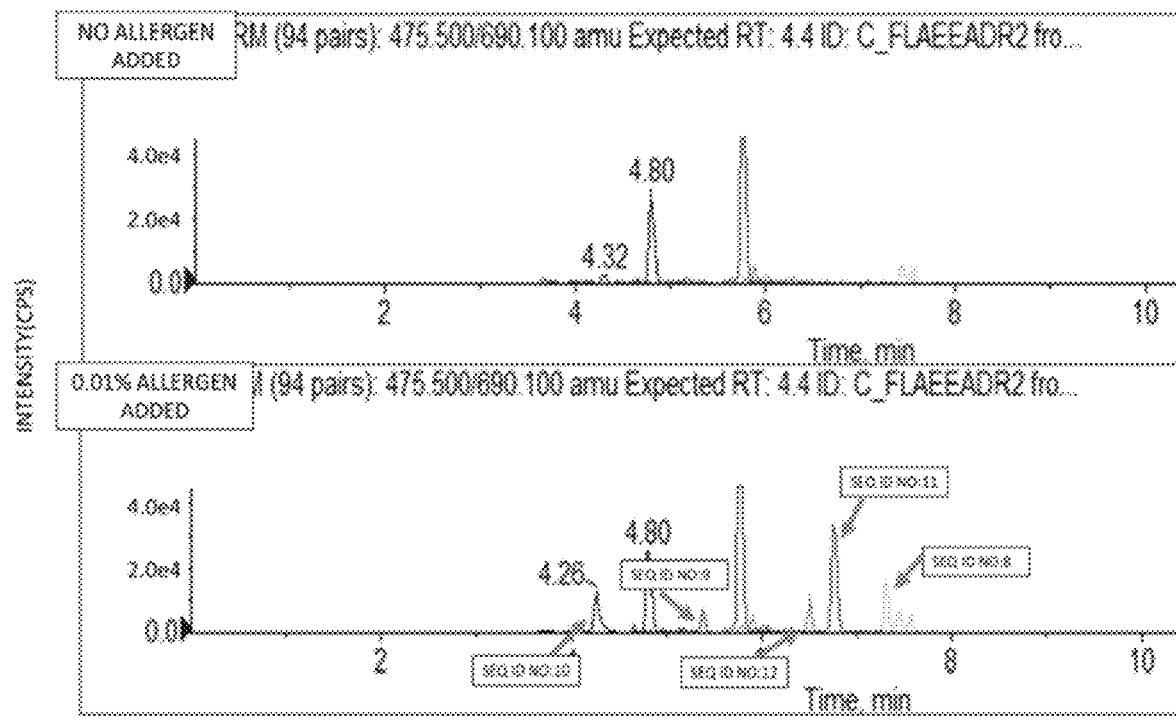

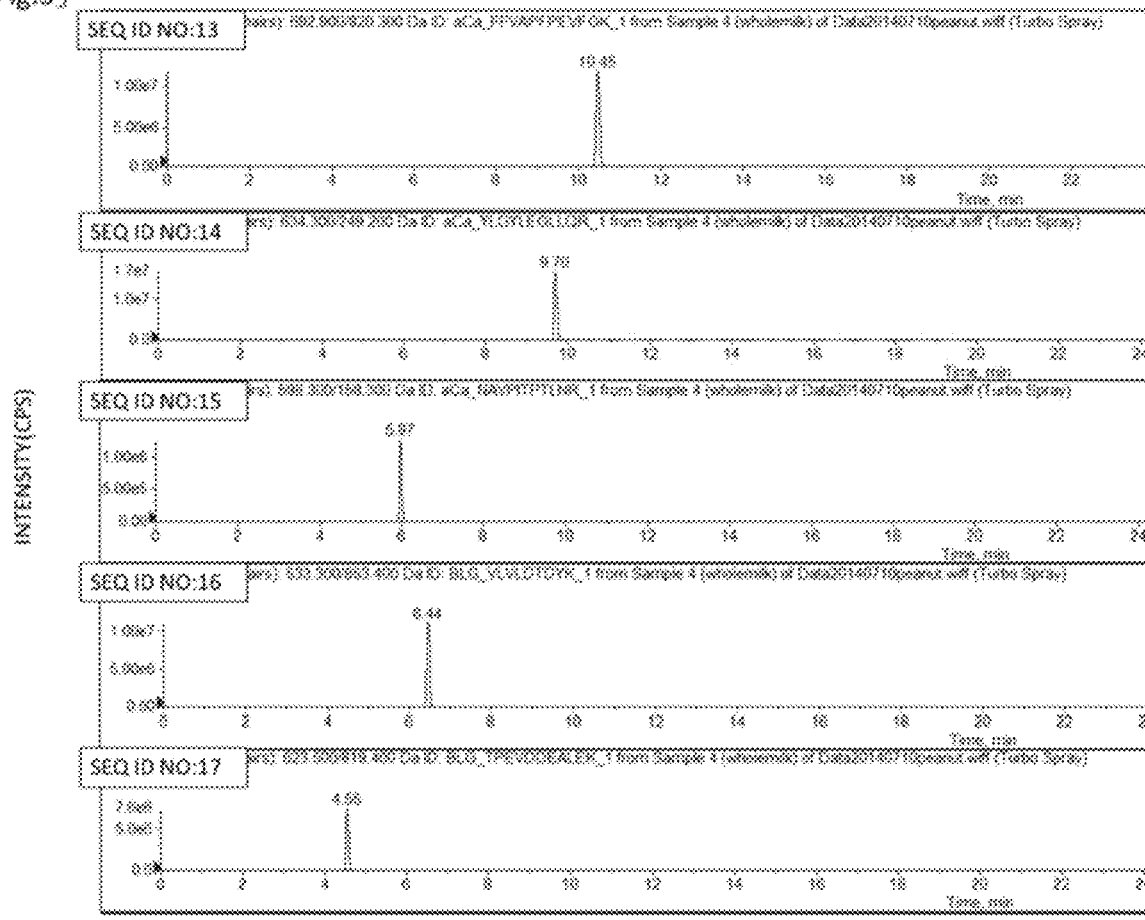

[Fig.6]
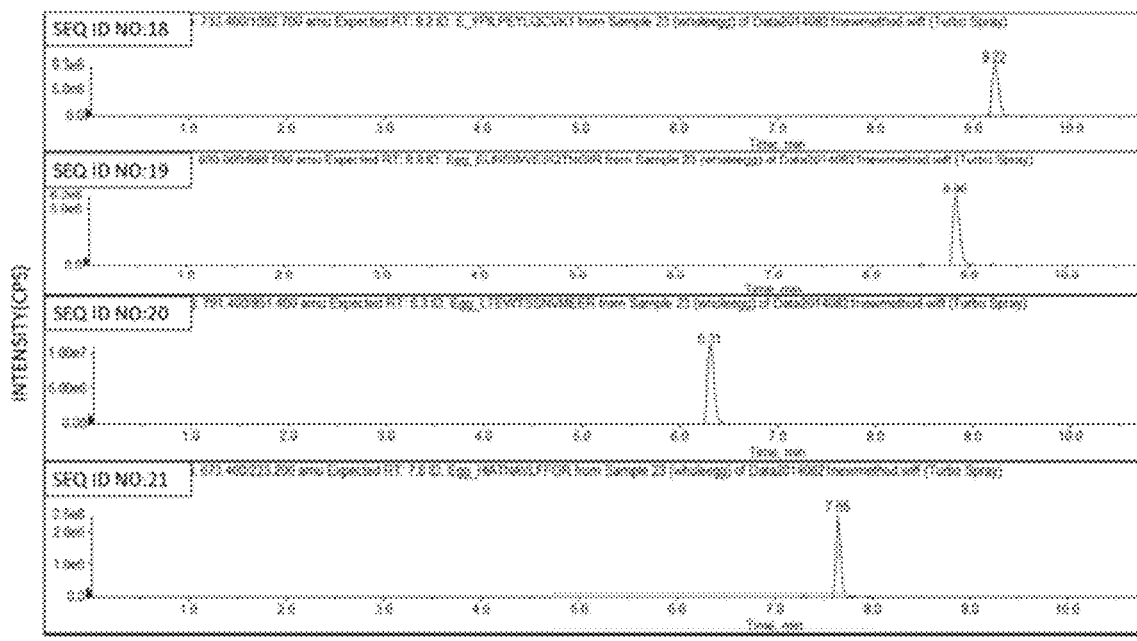
[Fig.7]
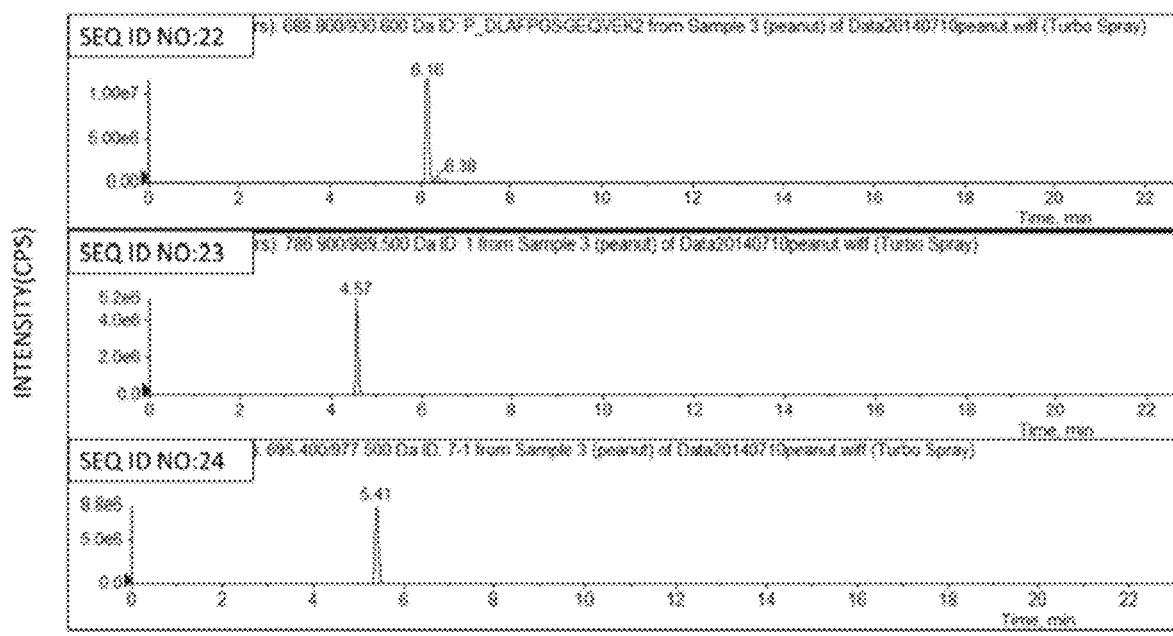

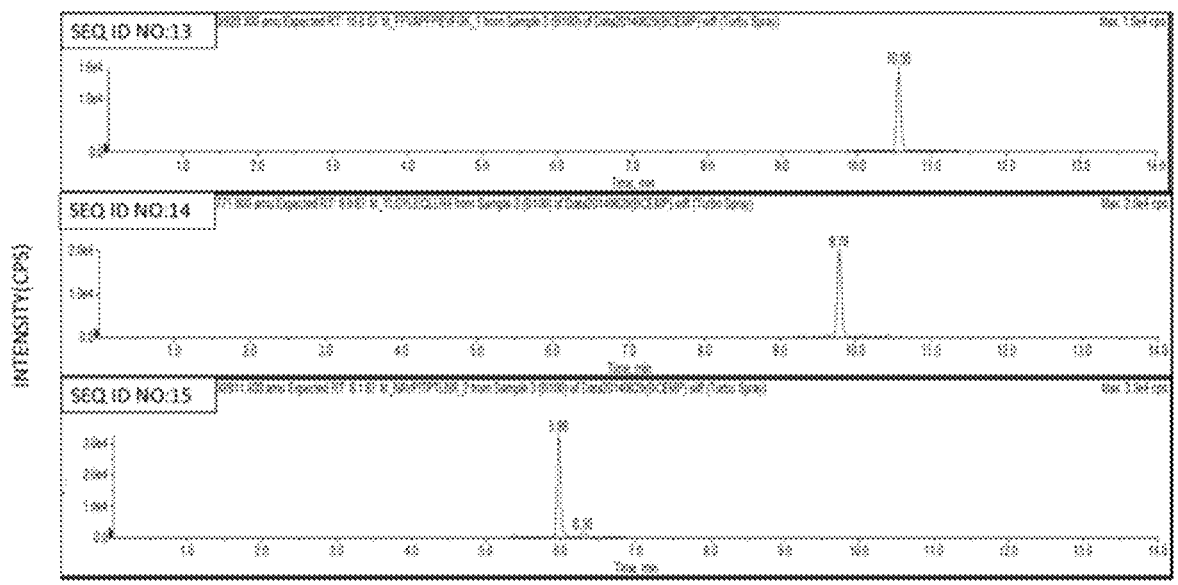
[Fig.8]
[Fig.9]

ALLERGEN DETECTION METHOD

TECHNICAL FIELD

The present invention relates to a method for detecting an allergen in a sample.

BACKGROUND ART

Food allergy causes disadvantageous symptoms such as dermatitis, asthma, gastrointestinal dysfunction and anaphylactic shock due to immune responses triggered by food. Various kinds of food cause food allergy. Among them, many patients are allergic to seven food types of shrimp, crab, wheat, buckwheat, egg, milk and peanut, and they are likely to cause severe allergic symptoms.

Even if a processed food product does not contain, as a raw material, any food that becomes the allergen, its final product may be contaminated with an allergen in some cases when a production line is shared with an allergen-containing processed food in a factory, or when an allergen is used in a process for manufacturing the raw material. Contamination with even a slight amount of allergen is dangerous for food allergic patients. A highly-sensitive-allergen-measurement method capable of detecting a trace amount of allergen in a sample such as a food product is required.

As the highly-sensitive-allergen-measurement method, Patent Literature 1 discloses a method for detecting the following allergen in a sample, including detecting a peptide having a specific sequence obtained by enzymatically cleaving the allergen by LC-MS/MS, wherein the allergen is selected from the group consisting of ovalbumin, lysozyme, casein, lactoglobulin, high molecular weight glutenin, low molecular weight glutenin, wheat protein, rye protein, oat protein, barley protein, mustardprotein, sesame protein, macadamia nut protein, pistachio nut protein, brazil nut protein, walnut protein, peanut protein and hazelnut protein. Patent Literature 2 discloses a method for measuring a content of allergen in a composition, including forming an extract containing an allergen from a sample composition, and measuring the amount of allergen in the extract using LC-UV/MS or LC-MS.

CITATION LIST

Patent Literature

Patent Literature 1: JP 2014-525588 A
Patent Literature 2: JP 2013-539039 A

SUMMARY OF INVENTION

Technical Problem

Detecting the presence of allergen (particularly buckwheat or crustacean) in a sample, such as a food product, with high sensitivity is needed.

Solution to Problem

The present inventor found that, by detecting a specific amino acid sequence contained in each allergen, the presence of the allergen can be detected with high sensitivity.

Accordingly, the present invention provides a method for detecting an allergen in a sample, the method comprising
treating the sample with a protease, and
detecting the presence or absence of an allergen-derived polypeptide in the enzymatically treated sample by chromatographic separation analysis,
wherein the allergen is one or more members selected from the group consisting of buckwheat, crustacean, milk, egg and peanut.

Advantageous Effects of Invention

The present invention provides a highly-sensitive-allergen-detection method capable of detecting the presence of a trace amount of allergen (particularly, buckwheat or crustacean) in a sample such as a food product.

BRIEF DESCRIPTION OF DRAWINGS

FIG. 1 is an LC-MS/MS analysis result on a trypsin digest of buckwheat allergen.
FIG. 2 is an LC-MS/MS analysis result on a trypsin digest of crustacean allergen.
FIG. 3 is an LC-MS/MS analysis result on a trypsin digest of buckwheat allergen-containing wheat flour. Top; wheat flour with no buckwheat allergen added, bottom; wheat flour with a buckwheat allergen added.
FIG. 4 is an LC-MS/MS analysis result on a trypsin digest of crustacean allergen-containing wheat flour. Top; wheat flour with no crustacean allergen added, bottom; wheat flour with a crustacean allergen added.
FIG. 5 is an LC-MS/MS analysis result on a milk allergen.
FIG. 6 is an LC-MS/MS analysis result on an egg allergen.
FIG. 7 is an LC-MS/MS analysis result on a peanut allergen.
FIG. 8 is an LC-MS/MS analysis result on casein in bread with milk added.
FIG. 9 is an LC-MS/MS analysis result on Ara h1 or h3 in bread with peanut added.

DESCRIPTION OF EMBODIMENTS

The present invention provides a method for detecting an allergen in a sample. According to the method of the present invention, one or more allergen members selected from the group consisting of buckwheat, crustacean, milk, egg and peanut can be detected. In a preferred embodiment, the allergen detected by the method of the present invention is one or more members selected from the group consisting of at least buckwheat and crustacean, more preferably one or more members selected from the group consisting of buckwheat and crustacean, still more preferably either buckwheat or crustacean. Alternatively, the allergen detected by the method of the invention includes at least buckwheat, and may be, for example, buckwheat alone, buckwheat and crustacean, or buckwheat, crustacean, milk, egg and peanut.

In the present invention, examples of an object to be subjected to allergen detection include a food product, cosmetic, medicine, raw material thereof, and instrument used in a manufacturing process thereof; however, the examples are not limited thereto. Such an object subjected to a conventional pretreatment, for example, grinding, dissolution, suspension, extraction, or a combination thereof, can be used as a sample for the method of the present invention. Alternatively, in a case where the object is an instrument, for example, its washing solution or wiped sample, or those subjected to grinding, dissolution, suspension, extraction etc., or a combination thereof can be used as a sample for the method of the present invention. A method for preparing the sample used in the method of the present invention is not limited to the above, and may include any method that can be used for preparing a sample for a protease treatment described below.

In the method of the present invention, the prepared sample is treated with a protease. Examples of the protease used in the method of the present invention include trypsin, chymotrypsin, elastase and thermolysin, preferably trypsin. Conditions for the treatment may be appropriately selected depending on the type of enzyme. For in a case of trypsin, the conditions preferably include an enzyme concentration of 1000 to 20000 U, temperature of 25 to 45° C., pH of about 7 to 9 and period of time of 4 to 24 hours. The enzymatic treatment cleaves a protein molecule of the target allergen to produce polypeptides derived from the allergen. Accordingly, if the target allergen is contained in a sample, the enzymatically treated sample contains polypeptides derived from the target allergen. On the other hand, if the target allergen is not contained in a sample, the enzymatically treated sample does not contain polypeptides derived from the target allergen.

Accordingly, it is possible to determine the presence or absence of the target allergen in a sample by detecting the presence or absence of a target allergen-derived polypeptide in the sample treated with the protease described above.

As to buckwheat, a cleavage product of a buckwheat 22 kDa protein molecule (SEQ ID NO: 25) can be detected as an allergen-derived polypeptide. In a preferred embodiment of the method of the present invention, in a case where the allergen is buckwheat, a polypeptide consisting of the amino acid sequence represented by any of SEQ ID NOs: 1 to 7 described below is detected as an allergen-derived polypeptide.

VQVVGDEGR (SEQ ID NO: 1)

SVFDDNVQR (SEQ ID NO: 2)

GQILVVPQGFAVVLK (SEQ ID NO: 3)

EGLEWVELK (SEQ ID NO: 4)

NFFLAGQSK (SEQ ID NO: 5)

GFIVQAR (SEQ ID NO: 6)

NDDNAITSPIAGK (SEQ ID NO: 7)

In the method of the present invention, the presence or absence of any one or more of polypeptides consisting of the amino acid sequences represented by above-described SEQ ID NOs: 1 to 7 may be detected. Preferably, the presence or absence of all of these polypeptides is detected.

As to crustacean such as crab and shrimp, a cleavage product of tropomyosin can be detected as an allergen-derived polypeptide. In a preferred embodiment of the method of the present invention, in a case where the allergen is crustacean, a polypeptides consisting of the amino acid sequence represented by any of SEQ ID NOs: 8 to 12 described below is detected as an allergen-derived polypeptide.

IQLLEEDLER (SEQ ID NO: 8)

MDALENQLK (SEQ ID NO: 9)

FLAEEADR (SEQ ID NO: 10)

IVELEEELR (SEQ ID NO: 11)

LAMVEADLER (SEQ ID NO: 12)

In the method of the present invention, the presence or absence of any one or more of polypeptides consisting of the amino acid sequences represented by above-described SEQ ID NOs: 8 to 12 may be detected. Preferably, the presence or absence of all of these polypeptides is detected.

In a case where the allergen is buckwheat and crustacean, the allergen-derived polypeptide to be detected is preferably any one or more of polypeptides consisting of the amino acid sequences represented by SEQ ID NOs: 1 to 7 and any one or more of polypeptides consisting of the amino acid sequences represented by SEQ ID NOs: 8 to 12, more preferably, all of the polypeptides consisting of the amino acid sequences represented by SEQ ID NOs: 1 to 12.

As to milk, a cleavage product of casein or β-lactoglobulin (BLG) can be detected as an allergen-derived polypeptide. In a preferred embodiment of the method of the present invention, in a case where the allergen is milk, a polypeptide consisting of the amino acid sequence represented by any of SEQ ID NOs: 13 to 17 described below is detected as an allergen-derived polypeptide. Among the following polypeptides, SEQ ID NOs: 13 to 15 are the amino acid sequences of casein-derived polypeptides, and SEQ ID NOs: 16 to 17 are the amino acid sequences of BLG-derived polypeptides.

FFVAPFPEVFGK (SEQ ID NO: 13)

YLGYLEQLLR (SEQ ID NO: 14)

NAVPITPTLNR (SEQ ID NO: 15)

VLVLDTDYK (SEQ ID NO: 16)

TPEVDDEALEK (SEQ ID NO: 17)

In the method of the present invention, the presence or absence of any one or more of polypeptides consisting of the amino acid sequences represented by above-described SEQ ID NOs: 13 to 17 is detected. Preferably, the presence or absence of all of these polypeptides is detected. As to casein, the presence or absence of preferably any one or more of polypeptides consisting of the amino acid sequences represented by SEQ ID NOs: 13 to 15, more preferably all of these polypeptides is detected. As to BLG, the presence or absence of preferably any one or more of polypeptides consisting of the amino acid sequences represented by SEQ ID NOs: 16 to 17, more preferably all of these polypeptides is detected.

As to egg, a cleavage product of ovalbumin can be detected as an allergen-derived polypeptide. In a preferred embodiment of the method of the present invention, in a case where the allergen is egg, a polypeptide consisting of the amino acid sequence represented by any of SEQ ID NOs: 18 to 21 described below is detected as an allergen-derived polypeptide.

YPILPEYLQCVK (SEQ ID NO: 18)

ELINSWVESQTNGIIR (SEQ ID NO: 19)

LTEWTSSNVMEER (SEQ ID NO: 20)

HIATNAVLFFGR (SEQ ID NO: 21)

In the method of the present invention, the presence or absence of any one or more of polypeptides consisting of the amino acid sequences represented by above-described SEQ ID NOs: 18 to 21 is detected. Preferably, the presence or absence of all of these polypeptides is detected.

As to peanut, a cleavage product of Ara h1-3 can be detected as an allergen-derived polypeptide. In a preferred embodiment of the method of the present invention, in a case where the allergen is peanut, a polypeptide consisting of the amino acid sequence represented by any of SEQ ID NOs: 22 to 24 described below is detected as an allergen-derived polypeptide. Among the following polypeptides, SEQ ID NOs: 22 to 23 are the amino acid sequences of Ara h1-derived polypeptides, and SEQ ID NO: 24 is the amino acid sequence of an Ara h3-derived polypeptide.

DLAFPGSGEQVEK (SEQ ID NO: 22)

VLLEENAGGEQEER (SEQ ID NO: 23)

SPDTYNPQAGSLK (SEQ ID NO: 24)

In the method of the present invention, the presence or absence of any one or more of polypeptides consisting of the amino acid sequences represented by above-described SEQ ID NOs: 22 to 24 is detected. Preferably, the presence or absence of all of these polypeptides is detected. As to Ara h1, the presence or absence of preferably any one or more of polypeptides consisting of the amino acid sequences represented by SEQ ID NOs: 22 to 23, more preferably all of these polypeptides is detected. As to Ara h3, the presence or absence of the polypeptide preferably consisting of the amino acid sequence represented by SEQ ID NO: 24 is detected.

Accordingly, when the allergen is buckwheat, crustacean, milk, egg and peanut, the allergen-derived polypeptide to be detected is preferably any one or more of the polypeptides consisting of the amino acid sequences represented by SEQ ID NOs: 1 to 7, any one or more of the polypeptides consisting of the amino acid sequences represented by SEQ ID NOs: 8 to 12, any one or more of the polypeptides consisting of the amino acid sequences represented by SEQ ID NOs: 13 to 17, any one or more of the polypeptides consisting of the amino acid sequences represented by SEQ ID NOs: 18 to 21, and any one or more of the polypeptides consisting of the amino acid sequences represented by SEQ ID NOs: 22 to 24; more preferably all of the polypeptides consisting of the amino acid sequences represented by SEQ ID NOs: 1 to 24.

As a means for detecting the presence or absence of the target allergen-derived polypeptide in the sample treated with the protease described above, a chromatographic separation analysis is preferable. Examples of the chromatographic separation analysis include liquid chromatography-mass spectrometry such as liquid chromatography tandem mass spectrometry (LC-MS/MS) or liquid chromatography time-of-flight mass spectrometry (LC-TOF/MS). Multiple reaction monitoring (MRM) using LC-MS/MS is preferable because it has high measurement accuracy (S/N ratio) and can detect multiple peptides at once.

In the method of the present invention, as the chromatography used for detection of the target allergen-derived polypeptide, liquid chromatography (LC) is preferable, and reversed phase liquid chromatography (RPLC) is more preferable. Also, the LC is preferably high performance liquid chromatography (HPLC), more preferably RP-HPLC. Examples of a carrier for RPLC include a carrier having a filler in which a hydrocarbon chain (preferably an octadecyl group) is bonded to silica gel or a polymer gel base material, such as a C18 column or C8 column. Any mobile phase (eluent) for the LC may be used as long as it is capable of individually separating the target allergen-derived polypeptides, and examples thereof includes, however is not limited to, a 100:0 to 0:100 (volume ratio) gradient solution of an aqueous solution of formic acid (A) and an aqueous solution of formic acid acetonitrile (B).

In liquid chromatography-mass spectrometry, the eluate from the LC is subjected to mass spectrometry (for example, MS/MS, TOF/MS). Mass spectrometry can be performed, under the usual conditions used in peptide detection, using a publicly known mass spectrometer, for example, tandem quadrupole mass spectrometer or time-of-flight mass spectrometer. For example, multiple reaction monitoring (MRM) using electrospray ionization (ESI) or atmospheric pressure chemical ionization (APCI) is preferred. In mass spectrometry, each polypeptide in the eluate is separated according to the mass/charge (m/z). For example, the presence or absence of the target polypeptide in a sample can be detected based on the measured m/z value by preliminarily making a database of the m/z value of the target polypeptide.

EXAMPLES

Hereinafter, a more detailed description of the present invention is made with reference to Examples; however, the present invention is not limited to the following Examples.

(Reagent)

Acetonitrile (Wako Pure Chemical Corporation, special grade, for HPLC)

Trypsin (Wako Pure Chemical Corporation, derived from porcine spleen, for biochemical analysis)

Iodoacetamide (IA) (Wako Pure Chemical Corporation, for biochemical analysis)

Dithiothreitol (DTT) (Wako Pure Chemical Corporation, for biochemical analysis)

Urea (Wako Pure Chemical Corporation, special grade)

Trifluoroacetic acid (TFA) (Junsei Chemical Co., Ltd., special grade)

(Buffer)

A: 0.1M DTT_0.5M Tris-HCl_4M urea (pH 8.2) buffer

B: 0.5M Tris-HCl_2M urea (pH 8.2) buffer

Reference Example 1 Preparation of Allergen-Containing Sample 0.5 g of a specimen was collected in a 15 mL disposable test tube, and 5 mL of Buffer A (Test Examples 1 to 3) or Buffer B (Test Examples 4 to 5) was added, followed by shake extraction for 3 hours (Test Examples 1 to 3) or 5 hours (Test Examples 4 to 5). The obtained reaction product was centrifuged at 3000 rpm for 5 minutes, and the supernatant was collected.

Example 1 Analysis of Trypsin Digest by LC-MS/MS

1) Trypsin Digestion 1 mg of allergen molecule or 0.25 mL of supernatant prepared in Reference Example 1 was collected in a polytube for 1.5 mL, and 0.25 mL of Buffer A (Test Examples 1 to 3) or Buffer B (Test Examples 4 to 5) was added for complete dissolution. To the obtained solution, 50 µL of 40 mg/mL DTT was added, followed by incubation at 37° C. for 90 minutes. Subsequently, 50 µL of 40 mg/mL IA was added, followed by incubation at 37° C. for 30 minutes in the absence of light. To the reaction solution, 600 µL of 50 mM sodium hydrogen carbonate was added, then 100 µL of a 10 mg/mL trypsin 50 mM sodium hydrogen carbonate solution was added, followed by incubation at 37° C. for 16 hours (pH 7 to 9). After the reaction, 10 µL of TFA was added for inactivation of trypsin.

2) Desalting

OASIS HLB (3 cc, 60 mg; Waters) was conditioned with 1 mL of methanol and 2 mL of water. To this, the whole amount of the reaction solution obtained in 1) was dropwise added, followed by washing with 1 mL of water and subsequent elution with 1 mL of 60% acetonitrile.

3) Multiple Reaction Monitoring (MRM) by LC-MS/MS

The eluate obtained in 2) was dried with nitrogen at 40° C., followed by dissolution in 0.2 mL of 25% acetonitrile. After the obtained solution was filtered, LC-MS/MS MRM was performed under the following conditions.

(Lc-Ms/Ms Apparatus)
HPLC: Shimadzu Nexera X2
MS/MS: AB SCIEX QTRAP 5500

(Hplc Conditions)
Column: Kinetik C 18 150 mm×2.1 mm, particle diameter 2.6 µm
Column temperature: 50° C.
Column flow rate: 0.3 mL
Eluent A: 0.1% formic acid; eluent B: 0.1% formic acid acetonitrile
Gradient: A:B 95:5 (0 min)→40:60 (20 min.)→20:80 (50 min)→95:5 (55 min) 95:5 (90 min)

(Mass Analysis Conditions)
Ionization method: electrospray ionization method
Polarity: Positive
Spray voltage: 5500 V
Turbo heater temperature: 450° C.

Test Example 1 Detection or Buckwheat Allergen

Using the 22 kDa protein (SEQ ID NO: 25) as a target allergen molecule, target allergen-derived polypeptides were detected by LC-MS/MS MRM under the condition shown in Table 1. The result is shown in FIG. 1.

TABLE 1

| DETECTED POLYPEPTIDE | MRM TRANSITION | |
|---|---|---|
| | Q1 | Q3 |
| VQVVGDEGR (SEQ ID NO: 1) | 479.5 | 632.1 / 533.0 |
| SVFDDNVQR (SEQ ID NO: 2) | 540.0 | 746.2 / 631.1 |
| GQILVVPQGFAVVLK (SEQ ID NO: 3) | 784.5 | 1057.8 / 958.6 |
| EGLEWVELK (SEQ ID NO: 4) | 551.6 | 674.3 / 488.1 |
| NFFLAGQSK (SEQ ID NO: 5) | 506.6 | 750.4 / 603.2 |
| GFIVQAR (SEQ ID NO: 6) | 395.9 | 586.2 / 473 |
| NDDNAITSPIAGK (SEQ ID NO: 7) | 658.2 | 786.4 / 673.2 |

Test Example 2 Detection of Crustacean Allergen

Using tropomyosin (SEQ ID NO: 26) as a target allergen molecule, target allergen-derived polypeptides were detected by LC-MS/MS MRM under the conditions shown in Table 2. The result is shown in FIG. 2.

TABLE 2

| DETECTED POLYPEPTIDE | MRM TRANSITION | |
|---|---|---|
| | Q1 | Q3 |
| IQLLEEDLER (SEQ ID NO: 8) | 629.2 | 1016.6 / 903.4 |
| MDALENQLK (SEQ ID NO: 9) | 531 | 815.2 / 744.1 |
| FLAEEADR (SEQ ID NO: 10) | 475.5 | 690.2 / 619.1 |
| IVELEEELR (SEQ ID NO: 11) | 565.1 | 917.5 / 788.4 |
| LAMVEADLER (SEQ ID NO: 12) | 573.6 | 1033.6 / 831.4 |

Test Example 3 Detection of Buckwheat Allergen and Crustacean Allergen from Food Composition From wheat flour to which 0.01% by mass of buckwheat or crustacean (shrimp powder) was added, an allergen-containing sample was prepared according to Reference Example 1. The obtained sample was subjected to trypsin digestion, desalting and LC-MS/MS MRM according to Example 1, with the result that the target allergen-derived polypeptides were detected. The same analysis was performed using wheat flour to which no buckwheat or crustacean was added as a control. The allergen-derived polypeptides detected and conditions of LC-MS/MS analysis for buckwheat and crustacean were the same as those described above for Tables 1 and 2, respectively. The measurement results are shown in FIGS. 3 and 4.

Test Example 4 Detection of Milk, Egg and Peanut Allergens

An allergen-containing sample was prepared according to Reference Example 1 from each of whole milk powder, whole egg powder and peanut flour. Each sample was subjected to trypsin digestion, desalting and LC-MS/MS MRM according to 1) to 3) in Example 1, with the result that the target allergen-derived polypeptides were detected. The target allergen molecules and detected allergen-derived polypeptides for each of the whole milk powder, whole egg powder and peanut flour are shown in Tables 3 to 5. All allergens of the whole milk powder, whole egg powder and peanut flour could be detected by LC-MS/MS analysis (FIGS. 5 to 7).

TABLE 3

MILK ALLERGEN

| TARGET ALLERGEN MOLECULE | DETECTED POLYPEPTIDE | MRM TRANSITION Q1 | Q3 |
|---|---|---|---|
| CASEIN | FFVAPFPEVFGK (SEQ ID NO: 13) | 692.9 | 920.3 991.3 |
|  | YLGYLEQLLR (SEQ ID NO: 14) | 634.3 | 249.2 991.3 |
|  | NAVPITPTLNR (SEQ ID NO: 15) | 598.3 | 158.3 911.4 |
| β-LACTOGLOBULIN (BLG) | VLVLDTDYK (SEQ ID NO: 16) | 533.3 | 853.4 — |
|  | TPEVDDEALEK (SEQ ID NO: 17) | 623.5 | 819.4 — |

TABLE 4

EGG ALLERGEN

| TARGET ALLERGEN MOLECULE | DETECTED POLYPEPTIDE | MRM TRANSITION Q1 | Q3 |
|---|---|---|---|
| OVALBUMIN | YPILPEYLQCVK (SEQ ID NO: 18) | 733.4 | 1092.7 979.5 |
|  | ELINSWVESQTNGIIR (SEQ ID NO: 19) | 930.0 | 888.5 1017.5 |
|  | LTEWTSSNVMEER (SEQ ID NO: 20) | 791.4 | 951.4 1052.5 |
|  | HIATNAVLFFGR (SEQ ID NO: 21) | 673.4 | 223.2 1095.6 |

TABLE 5

PEANUT ALLERGEN

| TARGET ALLERGEN MOLECULE | DETECTED POLYPEPTIDE | MRM TRANSITION Q1 | Q3 |
|---|---|---|---|
| Ara h1 | DLAFPGSGEQVEK (SEQ ID NO: 22) | 688.8 | 930.5 300.2 |
|  | VLLEENAGGEQEER (SEQ ID NO: 23) | 786.9 | 989.5 804.4 |
| Ara h3 | SPDIYNPQAGSLK (SEQ ID NO: 24) | 695.4 | 977.5 700.4 |

Test Example 5 Detection of Milk and Peanut Allergens from Food Composition

Bread to which either whole milk powder or peanut flour was added (added bread; additive amount of 0.84% by mass) and bread to which neither milk nor peanut was contained (non-added bread) were produced. The added bread and non-added bread were mixed to prepare 100-fold diluted added bread (additive amount of whole powdered milk and peanut flour of 0.0084% by mass). The concentration of a milk or peanut allergen (soluble protein of peanut containing casein and Ara h) contained in the obtained 100-fold diluted added bread was measured by ELISA (with lower limit of quantification of 1 ppm). The measurement result is shown in Table 6.

TABLE 6

| ALLERGEN | NON-ADDED BREAD (ppm) | ADDED BREAD (ppm) | 100-FOLD DILUTED ADDED BREAD (ppm) |
|---|---|---|---|
| MILK | N.D. | 625 | 6.5 |
| PEANUT | N.D. | 745 | 8.7 |

Next, allergen-containing samples were prepared, according to Reference Example 1, from non-added bread and 100-fold diluted added bread. The obtained samples were subjected to trypsin digestion, desalting and LC-MS/MS MRM according to Example 1, with the result that the target allergen-derived polypeptides were detected. As objects to be detected, casein-derived polypeptides (SEQ ID NOs: 13 to 15) were selected for milk, and Ara h1- or h3-derived polypeptides (SEQ ID NOs 22 to 24) were selected for peanut.

As a result, peaks of the milk allergen (casein) and peanut allergen (Ara h1 or h3) could be confirmed with sufficient sensitivity for the 100-fold diluted added bread (FIGS. 8 and 9). Furthermore, even when the LC-MS/MS MRM measurement was carried out similarly except for using a 500-fold diluted added bread, it was confirmed that the S/N of the peaks was 10 or more also. On the other hand, no peak was confirmed for the non-added bread. Therefore, according to the method of the present invention, an allergen can be detected with measurement sensitivity equivalent to that of ELISA (with lower limit of quantification of 1 ppm).

The invention claimed is:

1. A method for detecting an allergen in a sample, the method comprising
   treating the sample with a protease, thereby producing an enzymatically treated sample, and
   detecting the presence or absence of an allergen-derived polypeptide in the enzymatically treated sample by chromatographic separation analysis,
   wherein the allergen comprises buckwheat, and
   the allergen-derived polypeptide comprises any one or more of polypeptides consisting of amino acid sequences represented by SEQ ID NOs: 4 or 6.

2. The method according to claim 1, wherein the allergen comprises buckwheat and crustacean,
   wherein the allergen-derived polypeptide comprises any one or more polypeptides consisting of amino acid sequences represented by SEQ ID NOs: 4 or 6, and further comprises any one or more polypeptides with amino acid sequences selected from the group consisting of SEQ ID NOs: 8 to 12.

3. The method according to claim 1, wherein the allergen-derived polypeptide comprises any one or more polypeptides consisting of amino acid sequences represented by SEQ ID NOs: 4 or 6, and further comprises any one or more polypeptides with amino acid sequences selected from the group consisting of SEQ ID NOs: 1, 2, 3, 5, and 7.

4. The method according to claim 2, wherein the allergen-derived polypeptide comprises any one or more polypeptides consisting of amino acid sequences represented by SEQ NOs: 4 or 6, and further comprises any one or more polypeptides with amino acid sequences selected from the group consisting of SEQ ID NOs: 1, 2, 3, 5, and 7 to 12.

5. The method according to claim 1, wherein the chromatographic separation analysis is liquid chromatography tandem mass spectrometry.

6. The method according to claim 1, wherein the protease is trypsin.

* * * * *

SEQUENCE LISTING

<160> NUMBER OF SEQ ID NOS: 26

<210> SEQ ID NO 1
<211> LENGTH: 9
<212> TYPE: PRT
<213> ORGANISM: Fagopyrum esculentum

<400> SEQUENCE: 1

Val Gln Val Val Gly Asp Glu Gly Arg
1               5

```
<210> SEQ ID NO 2
<211> LENGTH: 9
<212> TYPE: PRT
<213> ORGANISM: Fagopyrum esculentum

<400> SEQUENCE: 2

Ser Val Phe Asp Asp Asn Val Gln Arg
1               5

<210> SEQ ID NO 3
<211> LENGTH: 15
<212> TYPE: PRT
<213> ORGANISM: Fagopyrum esculentum

<400> SEQUENCE: 3

Gly Gln Ile Leu Val Val Pro Gln Gly Phe Ala Val Val Leu Lys
1               5                   10                  15

<210> SEQ ID NO 4
<211> LENGTH: 9
<212> TYPE: PRT
<213> ORGANISM: Fagopyrum esculentum

<400> SEQUENCE: 4

Glu Gly Leu Glu Trp Val Glu Leu Lys
1               5

<210> SEQ ID NO 5
<211> LENGTH: 9
<212> TYPE: PRT
<213> ORGANISM: Fagopyrum esculentum

<400> SEQUENCE: 5

Asn Phe Phe Leu Ala Gly Gln Ser Lys
1               5

<210> SEQ ID NO 6
<211> LENGTH: 7
<212> TYPE: PRT
<213> ORGANISM: Fagopyrum esculentum

<400> SEQUENCE: 6

Gly Phe Ile Val Gln Ala Arg
1               5

<210> SEQ ID NO 7
<211> LENGTH: 13
<212> TYPE: PRT
<213> ORGANISM: Fagopyrum esculentum

<400> SEQUENCE: 7

Asn Asp Asp Asn Ala Ile Thr Ser Pro Ile Ala Gly Lys
1               5                   10

<210> SEQ ID NO 8
<211> LENGTH: 10
<212> TYPE: PRT
<213> ORGANISM: Marsupenaeus japonicus

<400> SEQUENCE: 8

Ile Gln Leu Leu Glu Glu Asp Leu Glu Arg
1               5                   10

<210> SEQ ID NO 9
<211> LENGTH: 9
```

```
<212> TYPE: PRT
<213> ORGANISM: Marsupenaeus japonicus

<400> SEQUENCE: 9

Met Asp Ala Leu Glu Asn Gln Leu Lys
1               5

<210> SEQ ID NO 10
<211> LENGTH: 8
<212> TYPE: PRT
<213> ORGANISM: Marsupenaeus japonicus

<400> SEQUENCE: 10

Phe Leu Ala Glu Glu Ala Asp Arg
1               5

<210> SEQ ID NO 11
<211> LENGTH: 9
<212> TYPE: PRT
<213> ORGANISM: Marsupenaeus japonicus

<400> SEQUENCE: 11

Ile Val Glu Leu Glu Glu Glu Leu Arg
1               5

<210> SEQ ID NO 12
<211> LENGTH: 10
<212> TYPE: PRT
<213> ORGANISM: Marsupenaeus japonicus

<400> SEQUENCE: 12

Leu Ala Met Val Glu Ala Asp Leu Glu Arg
1               5                   10

<210> SEQ ID NO 13
<211> LENGTH: 12
<212> TYPE: PRT
<213> ORGANISM: Bos taurus

<400> SEQUENCE: 13

Phe Phe Val Ala Pro Phe Pro Glu Val Phe Gly Lys
1               5                   10

<210> SEQ ID NO 14
<211> LENGTH: 10
<212> TYPE: PRT
<213> ORGANISM: Bos taurus

<400> SEQUENCE: 14

Tyr Leu Gly Tyr Leu Glu Gln Leu Leu Arg
1               5                   10

<210> SEQ ID NO 15
<211> LENGTH: 11
<212> TYPE: PRT
<213> ORGANISM: Bos taurus

<400> SEQUENCE: 15

Asn Ala Val Pro Ile Thr Pro Thr Leu Asn Arg
1               5                   10

<210> SEQ ID NO 16
<211> LENGTH: 9
<212> TYPE: PRT
<213> ORGANISM: Bos taurus
```

```
<400> SEQUENCE: 16

Val Leu Val Leu Asp Thr Asp Tyr Lys
1               5

<210> SEQ ID NO 17
<211> LENGTH: 11
<212> TYPE: PRT
<213> ORGANISM: Bos taurus

<400> SEQUENCE: 17

Thr Pro Glu Val Asp Asp Glu Ala Leu Glu Lys
1               5                   10

<210> SEQ ID NO 18
<211> LENGTH: 12
<212> TYPE: PRT
<213> ORGANISM: Gallus gallus

<400> SEQUENCE: 18

Tyr Pro Ile Leu Pro Glu Tyr Leu Gln Cys Val Lys
1               5                   10

<210> SEQ ID NO 19
<211> LENGTH: 16
<212> TYPE: PRT
<213> ORGANISM: Gallus gallus

<400> SEQUENCE: 19

Glu Leu Ile Asn Ser Trp Val Glu Ser Gln Thr Asn Gly Ile Ile Arg
1               5                   10                  15

<210> SEQ ID NO 20
<211> LENGTH: 13
<212> TYPE: PRT
<213> ORGANISM: Gallus gallus

<400> SEQUENCE: 20

Leu Thr Glu Trp Thr Ser Ser Asn Val Met Glu Glu Arg
1               5                   10

<210> SEQ ID NO 21
<211> LENGTH: 12
<212> TYPE: PRT
<213> ORGANISM: Gallus gallus

<400> SEQUENCE: 21

His Ile Ala Thr Asn Ala Val Leu Phe Phe Gly Arg
1               5                   10

<210> SEQ ID NO 22
<211> LENGTH: 13
<212> TYPE: PRT
<213> ORGANISM: Arachis hypogaea

<400> SEQUENCE: 22

Asp Leu Ala Phe Pro Gly Ser Gly Glu Gln Val Glu Lys
1               5                   10

<210> SEQ ID NO 23
<211> LENGTH: 14
<212> TYPE: PRT
<213> ORGANISM: Arachis hypogaea

<400> SEQUENCE: 23
```

Val Leu Leu Glu Glu Asn Ala Gly Gly Glu Gln Glu Arg
1               5                   10

<210> SEQ ID NO 24
<211> LENGTH: 13
<212> TYPE: PRT
<213> ORGANISM: Arachis hypogaea

<400> SEQUENCE: 24

Ser Pro Asp Ile Tyr Asn Pro Gln Ala Gly Ser Leu Lys
1               5                   10

<210> SEQ ID NO 25
<211> LENGTH: 183
<212> TYPE: PRT
<213> ORGANISM: Fagopyrum esculentum

<400> SEQUENCE: 25

Leu Lys Phe Arg Gln Asn Val Asn Arg Pro Ser Arg Ala Asp Val Phe
1               5                   10                  15

Asn Pro Arg Ala Gly Arg Ile Asn Thr Val Asp Ser Asn Asn Leu Pro
            20                  25                  30

Ile Leu Glu Phe Ile Gln Leu Ser Ala Gln His Val Leu Tyr Lys
        35                  40                  45

Asn Ala Ile Leu Gly Pro Arg Trp Asn Leu Asn Ala His Ser Ala Leu
    50                  55                  60

Tyr Val Thr Arg Gly Glu Gly Arg Val Gln Val Val Gly Asp Glu Gly
65                  70                  75                  80

Arg Ser Val Phe Asp Asp Asn Val Gln Arg Gly Gln Ile Leu Val Val
                85                  90                  95

Pro Gln Gly Phe Ala Val Val Leu Lys Ala Gly Arg Glu Gly Leu Glu
            100                 105                 110

Trp Val Glu Leu Lys Asn Asp Asp Asn Ala Ile Thr Ser Pro Ile Ala
        115                 120                 125

Gly Lys Thr Ser Val Leu Arg Ala Ile Pro Val Glu Val Leu Ala Asn
    130                 135                 140

Ser Tyr Asp Ile Ser Thr Lys Glu Ala Phe Arg Leu Lys Asn Gly Arg
145                 150                 155                 160

Gln Glu Val Glu Val Phe Arg Pro Phe Gln Ser Arg Asp Glu Lys Glu
                165                 170                 175

Arg Glu Arg Phe Ser Ile Val
            180

<210> SEQ ID NO 26
<211> LENGTH: 284
<212> TYPE: PRT
<213> ORGANISM: Marsupenaeus japonicus

<400> SEQUENCE: 26

Met Asp Ala Ile Lys Lys Lys Met Gln Ala Met Lys Leu Glu Lys Asp
1               5                   10                  15

Asn Ala Met Asp Arg Ala Asp Thr Leu Glu Gln Gln Asn Lys Glu Ala
            20                  25                  30

Asn Asn Arg Ala Glu Lys Ser Glu Glu Glu Val His Asn Leu Gln Lys
        35                  40                  45

Arg Met Gln Gln Leu Glu Asn Asp Leu Asp Gln Val Gln Glu Ser Leu
    50                  55                  60

```
Leu Lys Ala Asn Ile Gln Leu Val Glu Lys Asp Lys Ala Leu Ser Asn
65              70              75              80

Ala Glu Gly Glu Val Ala Ala Leu Asn Arg Arg Ile Gln Leu Leu Glu
                85              90              95

Glu Asp Leu Glu Arg Ser Glu Glu Arg Leu Asn Thr Ala Thr Thr Lys
            100             105             110

Leu Ala Glu Ala Ser Gln Ala Ala Asp Glu Ser Glu Arg Met Arg Lys
        115             120             125

Val Leu Glu Asn Arg Ser Leu Ser Asp Glu Glu Arg Met Asp Ala Leu
    130             135             140

Glu Asn Gln Leu Lys Glu Ala Arg Phe Leu Ala Glu Glu Ala Asp Arg
145             150             155             160

Lys Tyr Asp Glu Val Ala Arg Lys Leu Ala Met Val Glu Ala Asp Leu
            165             170             175

Glu Arg Ala Glu Glu Arg Ala Glu Thr Gly Glu Ser Lys Ile Val Glu
            180             185             190

Leu Glu Glu Glu Leu Arg Val Val Gly Asn Asn Leu Lys Ser Leu Glu
        195             200             205

Val Ser Glu Glu Lys Ala Asn Gln Arg Glu Glu Ala Tyr Lys Glu Gln
    210             215             220

Ile Lys Thr Leu Thr Asn Lys Leu Lys Ala Ala Glu Ala Arg Ala Glu
225             230             235             240

Phe Ala Glu Arg Ser Val Gln Lys Leu Gln Lys Glu Val Asp Arg Leu
            245             250             255

Glu Asp Glu Leu Val Asn Glu Lys Glu Lys Tyr Lys Ser Ile Thr Asp
            260             265             270

Glu Leu Asp Gln Thr Phe Ser Glu Leu Ser Gly Tyr
        275             280
```